US007638283B2

(12) United States Patent
Krafft et al.

(10) Patent No.: US 7,638,283 B2
(45) Date of Patent: Dec. 29, 2009

(54) AMYLOID β PROTEIN (GLOBULAR ASSEMBLY AND USES THEREOF)

(75) Inventors: Grant A. Krafft, Glenview, IL (US); William L. Klein, Winnetka, IL (US); Brett A. Chromy, Evanston, IL (US); Mary P. Lambert, Glenview, IL (US); Caleb E. Finch, Altadena, CA (US); Todd Morgan, Manhattan Beach, CA (US); Pat Wals, Los Angeles, CA (US); Irina Rozovsky, Pasadena, CA (US); Ann Barlow, Evanston, IL (US)

(73) Assignees: Northwestern University, Evanston, IL (US); University of Southern California, Los Angeles, CA (US)

( * ) Notice: Subject to any disclaimer, the term of this patent is extended or adjusted under 35 U.S.C. 154(b) by 541 days.

(21) Appl. No.: 11/130,566

(22) Filed: May 16, 2005

(65) Prior Publication Data

US 2006/0166275 A1 Jul. 27, 2006

Related U.S. Application Data

(63) Continuation of application No. 09/745,057, filed on Dec. 20, 2000, now abandoned, and a continuation of application No. 08/769,089, filed on Feb. 5, 1997, now Pat. No. 6,218,506.

(51) Int. Cl.
*G01N 33/53* (2006.01)
*A61K 38/00* (2006.01)
*A61K 51/00* (2006.01)

(52) U.S. Cl. .............................. 435/7.1; 514/2; 424/1.69
(58) Field of Classification Search .................. 435/7.1
See application file for complete search history.

(56) References Cited

U.S. PATENT DOCUMENTS 6,218,506 B1 4/2001 Krafft et al.

FOREIGN PATENT DOCUMENTS

WO    WO 9410569    *  5/1994

OTHER PUBLICATIONS

Namgung et al. 'Long Term Potentiation in Vivo in the Intact Mouse Hippocampus', Brain Research, vol. 689, pp. 85-92, 1995.*
Levine, Harry, 'Soluble Multimeric Alzheimer .Beta. (1-40) Pre-Amyloid Complexes in Dilute Solution', Neurobiology of Aging, vol. 16, No. 5, pp. 755-764, 1995.*
Database CAPLUS on STN. No. 1993:623304. Chauhan et al. 'Dual Modulation of Protein Kinase C Activity by Amyloid Beta-Protein', abstract, 1993.*
Roher et al. (Biochem., 90, 10836-10840) (both cited in the IDS of Dec. 10, 2007 (cited in applicant's IDS).*
Kuo, Yu-Min, Emmerling, Mark R., Vigo-Pelfrey, Carmen, Kasunic, Timothy C., Kirkpatrick, Joel B., Murdoch, Geoffrey H., Ball, Melvyn J., Roher, Alex E., (1996). Water-soluble Aβ (N-40, N-42) Oligomers in Normal and Alzheimer Disease Brains. *The Journal of Biological Chemistry*, 271(8), 4077-4081.
Roher, Alex E., Lowenson, Jonathon, D., Clarke, Steven, Woods, Amina S., Cotter, Robert J., Gowing, Eric, Ball, Melvyn, J. (1993). β-Amyloid-(1-42) is a major component of cerebrovascular amyloid deposits: Implication for the pathology of Alzheimer disease. *Biochemistry*, 90, 10836-10840.
Roher, Alex E., Chaney, Michael O., Kuo, Yu-Min, Webster, Scott D., Stine, W. Blaine, Haverkamp, Lanny J., Woods, Amina S., Cotter, Robert J., Thouhy, James M., Krafft, Grant A., Bonnell, Barry S., Emmerling, Mark R., (1996) Morphology and toxicity of Aβ-(1-42) Dimer Derived from Neuritic and Vascular Amyloid Deposits of Alzheimer's Disease. *The Journal of Biological Chemistry*, 271(34), 20631-20635.
Wisniewski, T., Ghiso, J., Frangione, B., (1994). Alzheimer's Disease and Soluble Aβ. *Neurobiology of Aging*, 15(2), 143-152.
Busciglio, J., Lorenzo, A., Yeh., J., and Yanker, B.A. (1995). β-Amyloid Fibrils Induce Tau Phosphorylation and Loss of Microtubule Binding. *Neuron* 14, 879-888.
Cal, X.D., Golde, T.E., and Younkin, S.G. (1993). Release Of Excess Amyloid Beta Protein From a Mutant Amyloid Beta Protein Precursor. *Science* 259, 514-516.
Chartier-Harlan, M.C., Crawford, F., Houlden, H., Warren, A., Hughes, D., et al (1991) Early-onset Alzheimer's Disease Caused by Mutations at Codon 717 of the β-Amyloid Precursor Protein *Nature*, 353, 844-6.
Citron, M., Oltersdorf, T., Haass, C., McConlogue, L., Hung, A. Y., Seubert, P., Vigo-Pelfrey, C., Lieberburg, I., Selkoe, D. (1992). Mutation Of the Amyloid Precursor Protein in Familial Alzheimer's Disease Increases Beta Protein Production. *Nature* 360, 672-674.

(Continued)

*Primary Examiner*—Maury Audet
(74) *Attorney, Agent, or Firm*—Licata & Tyrrell P.C.

(57) ABSTRACT

The invention described in this disclosure involves a new composition of matter, amyloid beta-derived dementing ligands (ADDL's). ADDLs consist of amyloid β peptide assembled into soluble globular non-fibrillar oligomeric structures that are capable of activating specific cellular processes. The invention further encompasses methods for assaying the formation, presence, receptor protein binding and cellular activities of ADDLs. The invention further encompasses assay methods and inhibitor molecules for cellular signaling molecules activated by ADDLs. Also described are molecules that block proteins that promote the formation of ADDLs.

2 Claims, 4 Drawing Sheets

OTHER PUBLICATIONS

Esch, F. S., Keim, P. S., Beattie, E. C., Blacher, R. W., Culwell, A. R., Oltersdorf, T., McClure, D., Ward, P. J. (1990). Cleavage Of Amyloid Beta Peptide During Constitutive Processing Of Its Precursor *Science* 248, 1122-1124.

Glenner, G. G., and Wong, C. W. (1984a). Alzheimer's Disease Initial Report Of the Purification and Characterization Of a Novel Cerebro Vascular Amyloid. *Biochem Biophys Res Commun* 120, 885-890.

Glenner, G. G., and Wong, C. W. (1984b). Alzheimer's Disease and Downs Syndrome Sharing Of a Unique Cerebrovascular Amyloid Fibril Protein. *Biochem Biophys Res Commun* 122, 1131-1135.

Goate, A., Chartier-Harlen, M. C., Mullen, M., Brown, J., Crawford, F., et at (1991) Segregation of a Missense Mutation in the Amyloid Precursor Protein Gene with Familial Alzheimer's Disease. *Nature*, 349, 704-6.

Iversen, L. L, Mortishire-Smith, R. J., Pollack, S. J., Shearman, M. S. (1995). The toxicity in vitro of β-amyloid protein. *Biochem* 311, 1-16.

Kang, J., Lemaire, H.G., A. Unterbeck, J. Salbaum, C. Masters, K.-H. Grzeschik, G. Multhaup, K. Beyreuther, B. Muller-Hill (1987) *Nature* 325, 733-736.

Ladror, U. S., Snyder, S. W., Wang, G. T., Holzman, T. F., Krafft, G. A. (1994) "Cleavage at the Amino and Carboxy Termini of Alzheimer's Amyloid-β by Cathepsin D" *J. Biol. Chem.* 269, 18422-8.

Ladu, M. J., Falduto, M. T., Manelli, A. M., Reardon, C. A., Getz, G. S., Frail, D. E. lsoform-Specific Binding of Apolipoprotein-E to Beta-Amyloid. (1994) *J. Biol. Chem.* 269, 23403-23406.

Ladu, M. J., Falduto, M. T., Manelli, A. M., Reardon, C. A., Getz, G. S., and Frail, D. E. (1994) Purification of Apolipoprotein-E Attenuates Isoform-Specific Binding to Beta-Amyloid. *J. of Biol. Chem.* 269, 9039-9042.

Lambert, M. P., Stevens, G., Sabo, S., Barber, K., Wang, G., Wade, W., Krafft, G., Snyder, S., Holzman, T. F., Klein, W. L. (1994) b/A4-Evoked Degeneration of Differentiated SH-Sy5Y Human Neuroblastoma Cells. *J. Neurosci. Res.* 39, 377-384.

Levy-Lahad E., Wijsman EM, Nemens E, Anderson L, Goddard Kab, Weber JL, Bird TD, Schellenberg GD (1995) a Familial Alzheimer's Disease Locus on Chromosome 1. *Science* 269: 970-973.

Lorenzo, A., and Yankner, B. A. (1994). β-Amyloid neurotoxicity requires fibril information and is inhibited by Congo red. *Proc Natl Acad Sci* 91, 12243-12247.

Ma J, Yee A, Brewer HB, Das S and Potter H (1994) The amyloid-associated proteins a1-antichymotrypsin and apolipoprotein E promote the assembly of the Alzheimer β-protein into filaments. *Nature* 372: 92-94.

Mann, D. M., lwatsubo, T., Cairns, N. J., Lantos, P. L., Nochlin, D., Sumi, S. M., Bird, T. D., Poorkaj, P., Hardy, J., Hutton, M., Prihar, G., Crook, R., Rossor, M. N., and Haltia, M. (1996). Amyloid beta protein (Abeta) deposition in chromosome, 14-linked Alzheimer's disease: predominance of Abeta42(43). *Annals of Neurology* 40, 149-56.

Masters, C.L., Multhaup, G., Simms, G., Pottgiesser, J., and Martins, R. (1985a). Neuronal Origin Of a Cerebral Amyloid. Neurofibrillary Tangles Of Alzheimer's Disease Contain the Same Protein As the Amyloid Of Plaque Cores and Blood Vessels. *EMBO J.* 4, 2757-2764.

Masters, C.L., Simms, G., Weinman, N.A., Multhaup, G., and McDonald, B. (1985b). Amyloid Plaque Core Protein In Alzheimer's Disease and Down Syndrome. *Proc Natl Acad Sci U S A* 82, 4245-4249.

May, P. C., Gitter, B. D., Waters, D. C., Simmons, L. K., Becker, G. W., Small, J. S., and Robison, P. M. (1992). β-Amyloid Peptide In Vitro Toxicity: Lot-to-Lot Variability. *Neurobiol Aging* 13, 605-607.

Mullan, M., Crawford, F. Axelman, K., Houlden, H., Lilius, L. Winblad, B., Lannfelt, L. (1992) A Pathogenic Mutation for Probable Alzheimer's-Disease in the APP Gene at the N-Terminus of Beta-Amyloid. Nature Genetics 1, 345-347.

Murrell, J. Farlow M., Ghetti, B., and Benson, M.D. (1991). A mutation in the Amyloid Precursor Protein Associated with Hereditary Alzheimer's Disease. *Science*, 254, 97-9.

Namgung, U., Valcourt, E., Routtenberg A. (1995). Long-term potentiation in vivo in the intact mouse hippocampus. *Brain Research* 689, 85-92.

Oda, T., Pasinetti, G. M., Osterburg, H. H., Anderson, C., Johnson, S.A., Finch, C.E. (1994). Purification and Characterization of Brain Clusterin. *Biochem. Biophys. Res. Commun.*, 204, 1131-1136.

Oda, T., Pasinetti, G. M., Stine, W. B., Snyder, S. W., Holzman, T. F., Krafft, G. A., Osterburg, H. H., Johnson, S. A., Finch, C. E. (1995). Clusterin (apoJ) Alters the Aggregation of Amyloid β-Peptide ($A\beta_{1-42}$) and Forms Slowly Sedimenting Aβ/Clusterin complexes that cause Oxidative Stress *Exptl. Neurology*, 136, 22-31.

Pike, C. J., Burdick, D., Walencewicz, A. J., Glabe, C. G., and Cotman, C. W. (1993). Neurodegeneration Induced by β-Amyloid Peptides in vitro: The Role of Peptide Assembly State. *The Journal of Neuroscience* 13(4), 1676-1687.

Roher, A. E., Palmer, K.C., Yurewicz, E. C., Ball, M. J., Greenberg, B. D., Strittmatter, W. J., Huang, D. Y., Bhasin, R., Roses, A. D., and Goldgaber, D. (1993). Morphological and biochemical analyses of amyloid plaque core proteins purified from Alzheimer's disease brain tissue. *Neurochem* 61, 1916-1926.

Scheuner, D., Eckman, C., Jensen, M., Song, X., Citron, M., Suzuki, N., Bird, T. D., Hardy, J., Hutton, M., Kukull, W., Larson, E., Levy-Lahad, E., Viitanen, M., Peskind, E., Poorkaj, P., Schellenberg, G., Tanzi, R., Wasco, W., Lannfelt, L., Selkoe, D., and Younkin, S. (1996). Secreted amyloid beta-protein similar to that in the senile plaques of Alzheimer's disease is increased in vivo by the presenilin 1 and 2 and APP mutations linked to familial Alzheimer's disease. *Nature Medicine* 2, 864-70.

Selkoe, D. J. (1994). Normal and abnormal biology of the beta-amyloid precursor protein. Cowan, W. M. (Ed.). *Annual Review of Neuroscience*, vol. 17. ix + 623p. Annual Reviews Inc.: Palo Alto, California, USA., 489-517.

Sherrington R, et al., (1995) Cloning a gene bearing missense mutations in early onset familial Alzheimer's disease. *Nature* 375: 754-760.

Simmons, L. K., May, P. C., Tomaselli, K. J., Rydel, R. E., Fuson, K. S., Brigham, E. F., Wright, S., Lieberburg, I., Becker, G. W., Brems, D. N., and Li, W. Y. (1994). Secondary Structure of Amyloid β Peptide Correlates with Neurotoxic Activity In Vitro. *Molecular Pharmacology* 45, 373-379.

Sisodia, S. S., Koo, E. H., Beyreuther, K., Unterbeck, A., and Price, D. L. (1990). Evidence That Beta Amyloid Protein In Alzheimer's Disease Is Not Derived By Normal Processing. *Science* 248, 492-495.

Snow, A. D., Sekiguchi, R. T., Nochlin, D., Kimata, K. (1992). A Rat Model to Study the Effects of BAP-Containing Amyloid in Brain. ("Brain amyloid accumulation in rats within 1 week of infusion of amyloid-β and a plaque component") (1992) *Soc. Neurosci. Abstr.* 18, 1465, Ab. 616.6.

Snyder, S. W. Ladror, U. L., Wade. W. S., Wang, G. T., Barrett. L. W., Matayoshi, E. D., Huffaker, J. J. Krafft, G. A., Holzman, T. F. (1994) Amyloid β Aggregation: Selective Inhibition of Aggregation in Mixtures of Amyloid with Different Lengths. *Biophys. J.* 67, 1216-28.

Strittmatter, W. J., Saunders, A. M., Schmechel, D., Pericak-Vance, M., Enghild, J., Salvesen, G. S., Roses, A. D. (1993). Apolipoprotein E: High-avidity binding to β-amyloid and increased frequency of type 4 allele in late-onset familial Alzheimer disease. *Proc Natl Aced Sci* 90, 1977-1981.

Suzuki, N., Cheung, T. T., Cai, X. D., Odaka, A., Otvos, L., Jr., Eckman, C., Golde, T. E., and Younkin, S. G. (1994). An increased percentage of long amyloid β protein secreted by familial amyloid protein precursor (beta-APP-717) mutants. *Science* 264, 1336-1340.

Tamaoka, A. Kondo. T., Odaka, A. Sahara, N., Sawamura, N., Ozawa, K., Suzuki, N., Shoji, S. Mori, H., (1994) Biochemical Evidence for the Long-Tail Form (Aβ-1-42-43) of Amyloid-Beta Protein as a Seed Molecule in Cerebral Deposits of Alzheimer's Disease *Biochem. Biophys. Res. Commun.* 205, 834-842.

Tanzi, R. E., Gusella, J. F., Watkins, P. C., Bruns, G. A. P., St. George-Hyslop, P. H., van Keuren, D., Patterson, D., Pagan, S., Kurnit, D. M., and Neve, R. L. (1987). Amyloid Beta Protein Gene Complementary DNA, mRNA Distribution and Genetic Linkage Near the Alzheimer Locus. *Science* 235, 880-884.

Wright C. I., Geula C., and Mesulam M. M. (1993) Neuroglial cholinesterases in the normal brain and in Alzheimer's Disease: relationship to plaques, tangles and patterns of selective vulnerability. *Ann Neurol* 34, 373-384.

Yankner, B. A. (1996). Mechanisms of Neuronal Degeneration in Alzheimer's Disease. *Neuron* 16, 921-932.

Zhang, C., Lambert, M. P., Bunch, C., Barber, K., Wade, W. S., Krafft, G. A., and Klein, W. L. (1994). Focal Adhesion Kinase Expressed by Nerve Cells Lines Shows Increased Tyrosine Phosphorylation in Response to Alzheimer's A$\beta$ Peptide. *The Journal of Biological Chemistry* 269, 25247-25250.

\* cited by examiner

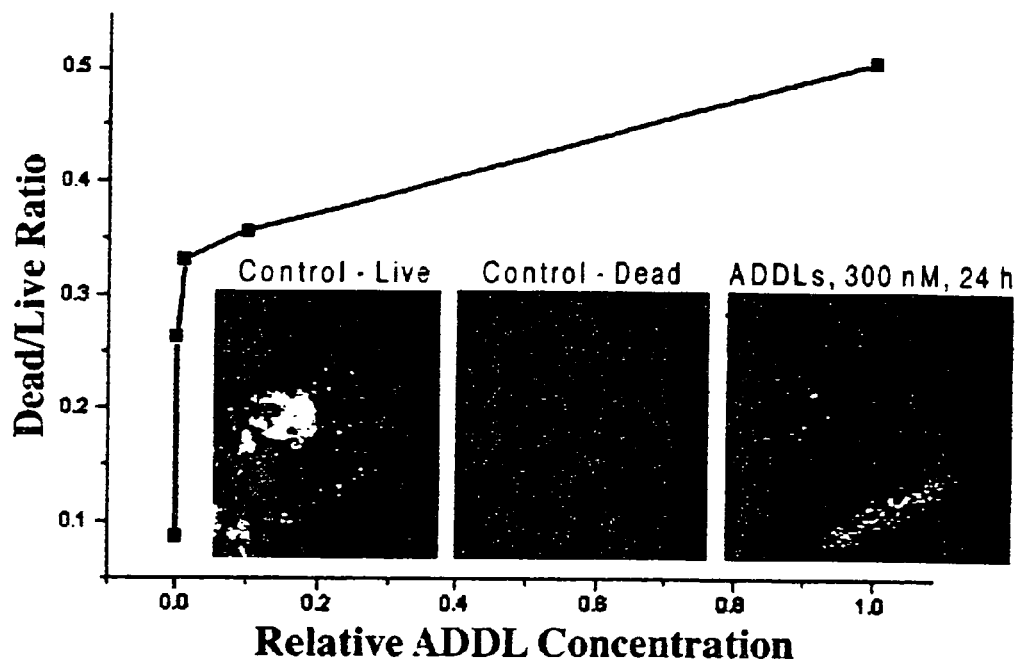
Figure 1. Neurotoxicity of ADDLs in organotypic hippocampal brain slices after ADDL treatment for 24 h, using the Dead/Live™ red/green fluorescence assay. Dose response curve represents a 1000-fold dilution from initial Aβ concentration of 1.7 µM, ADDL concentration of ca. 300 nM.

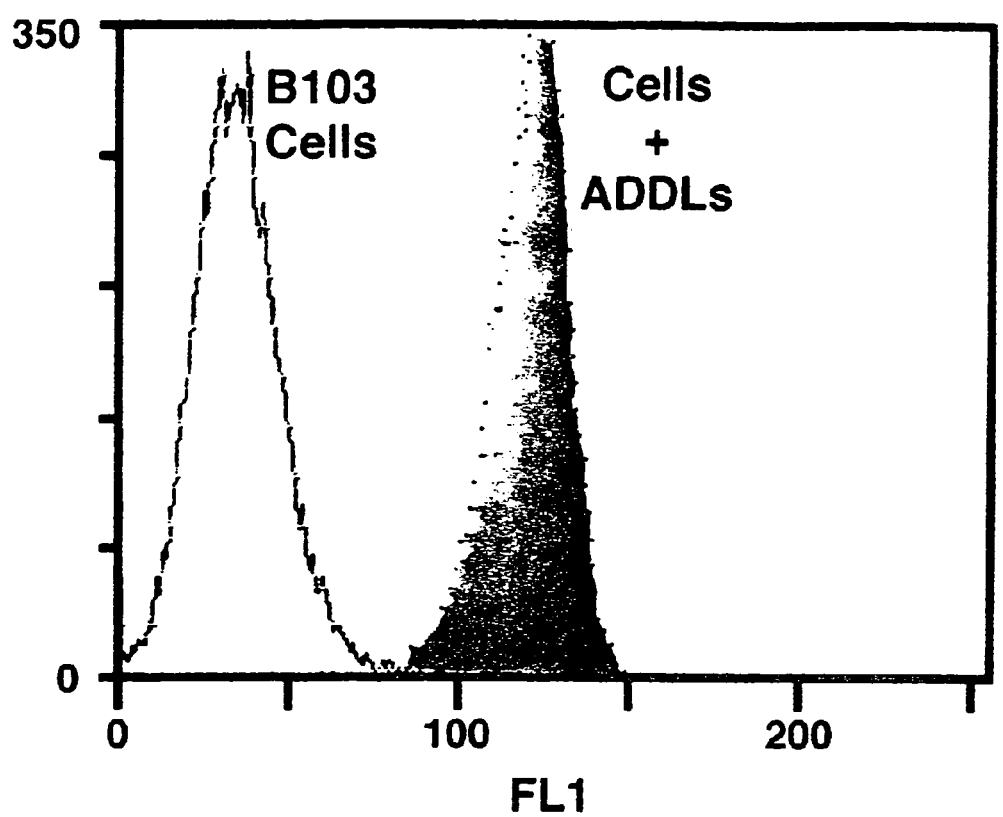
Figure 2. Analysis of binding of fluorescent labeled ADDLs to the surface of B103 rat CNS neuroblastoma cells using a fluorescence-activated cell sorter (FACS).

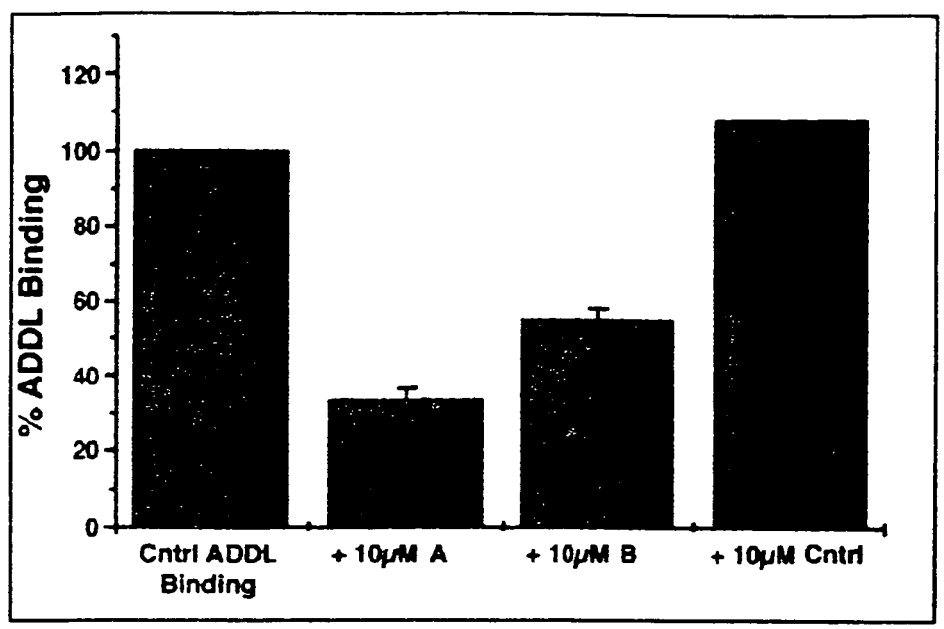
Figure 3. FACS assay identifies 2 compounds that block binding to B103 cells. Compound A is Aβ 1-40.

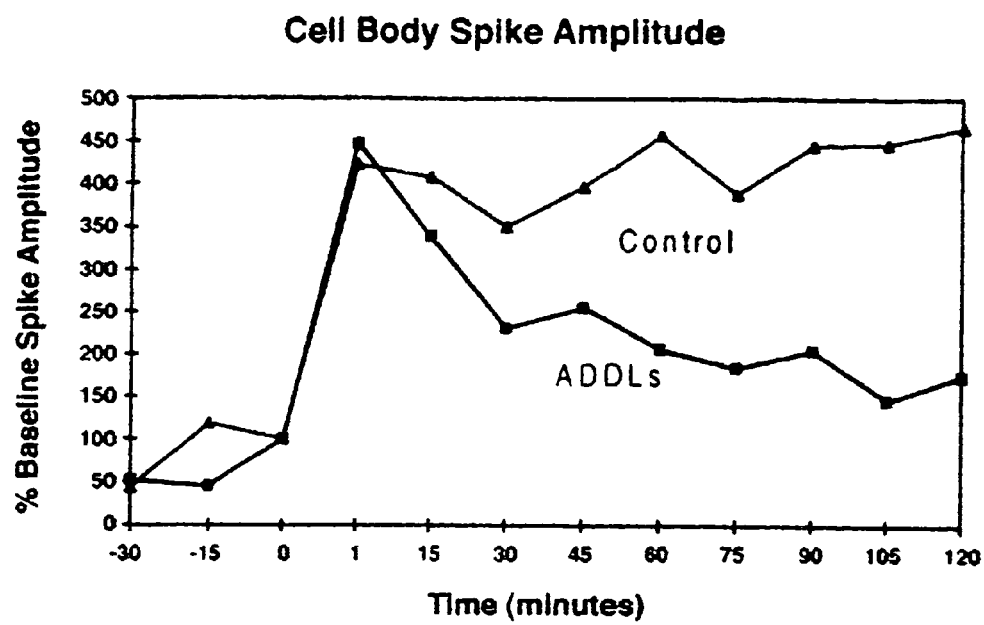
Figure 4. ADDLs block the persistence phase of LTP induced by high frequency electrical stimuli applied to entorhinal cortex and measured as cell body spike amplitude in middle molecular layer of the dentate gyrus.

ns
AMYLOID β PROTEIN (GLOBULAR ASSEMBLY AND USES THEREOF)

RELATED APPLICATIONS

This is a continuation of application Ser. No. 09/745,057 filed Dec. 20, 2000, now abandoned.

This application is a continuation of U.S. patent application Ser. No. 8,769,089, filed Feb. 5, 1997, now U.S. Pat. No. 6,218,506.

BACKGROUND OF THE INVENTION

1. Field of Invention

This invention is related to amyloid β proteins and detection, prevention and treatment of Alzheimer's disease.

2. Background of the Prior Art

Alzheimer's disease is a progressive neurodegenerative disease, characterized by distinct pathologies, including neurofibrillary tangles, neuritic plaques, neuronal atrophy, dendritic pruning and neuronal death. Neurofibrillary tangles represent the collapsed cytoskeleton of dead and dying neurons, while neuritic plaques are extracellular deposits of various protein, lipid, carbohydrate and salt components, the primary protein component of which is a 39-43 residue peptide known as amyloid β. Historically, it is these pathologic hallmarks that have defined Alzheimer's disease, rather than a distinct cellular or physiologic mechanism. Undoubtedly, there are specific operative mechanisms responsible for most of what we currently call Alzheimer's disease; however, these mechanisms very likely operate within a background environment that variously affords some level of protection, or exerts contributing and exacerbating effects. The result is a very broad age/incidence distribution curve, with few clues from population studies that point to specific causes.

One of the significant recent successes has been the identification of specific mutations in proteins on chromosome 14 (Sherington et al., 1995) and chromosome 1 (Levy-Lahad et al., 1995) that are linked to hereditary Alzheimer's disease, augmenting earlier findings involving two different sites of mutations in the APP gene. All of these mutations have now been shown to converge into a final common causative pathway for Alzheimer's disease that involves elevated levels of amyloid β-42/3, the long form of Aβ that is found prevalently in AD plaques because it is highly prone to rapid aggregation in aqueous media.

Amyloid β in Alzheimer's Disease. The molecular era in Alzheimer's research dates to 1984, when Glenner and Wong (1984a) succeeded in isolating and identifying the cerebrovascular amyloid associated with Alzheimer's disease. Subsequently, Glenner and Wong (1984b) and Masters et. al. (1985ab) identified the same 39-43 residue peptides now known as amyloid β, as the major protein component of Alzheimer's disease neuritic plaques. This represented the first time a discrete molecule had been linked to Alzheimer's disease, a disease which to that point had been characterized only by neuroanatomy and neuropathology descriptions. Amyloid β also was identified as the plaque component in brains of Down's Syndrome individuals, (Glenner and Wong 1984b, Masters 1984b), leading to the suggestion that the gene encoding it might exist on chromosome 21. By 1987, a number of groups had used the amyloid β sequence information and molecular genetics techniques to validate that suggestion, identifying the gene for the amyloid precursor protein (APP). (Kang et al., 1987, Tanzi et al., 1987).

The APP gene is a large, multi-exon gene that is differentially spliced into a number of APP's (reviewed in Selkoe, 1994). The proteins are large transmembrane proteins, now known to be processed by several pathways, one or more of which may generate amyloid β. The earliest studies of APP processing had suggested that amyloid β formation was not a normal process (Esch et al., 1990, Sisodia et al., 1990), though subsequent studies in cultured cells and analysis of serum and cerebrospinal fluid have shown that amyloid β formation occurs as a normal process in many cell types, though its formation may not represent a predominant overall pathway.

Pivotal genetic studies of DNA from individuals afflicted with early onset of familial Alzheimer's disease revealed that mutations in a single gene, this same APP gene, were causative for this very severe form of the disease. Interestingly, several different mutations in the APP gene were found including three different single residue substitutions at Val 717, four residues downstream of the amyloid β 1-42 C-terminus (Goate et al., 1991, Chartier-Harlan, et al., 1991, Murrell, et al., 1991), and a two residue mutation (670-671) immediately upstream of the amyloid β N-terminus, associated with early onset familial Alzheimer's disease in a Swedish family (Mullan, et al., 1992). When a vector encoding the cDNA of the Swedish mutant APP gene was transfected into cell lines to evaluate APP processing, it was found that six-eight times more amyloid β was formed, when compared with levels from wild-type APP (Citron, et al., 1992, Cai et al., 1993). It has also demonstrated that brain tissue extracts containing native human brain protease activities were able to process a fluorogenic octapeptide substrate encompassing the Swedish mutation more than 100-fold faster than the corresponding substrate based on the wild-type sequence (Ladror, et al., 1994). These results suggest that the mechanism by which the Swedish mutation causes early onset familial Alzheimer's disease involves substantial overproduction of amyloid β. Similar studies of amyloid formation in cells transfected with the 717 mutant APP also had been conducted, but the levels of amyloid β produced were not different from levels produced by wild-type APP. This led to mechanistic speculations that something other than amyloid β production was pathogenic for these mutations. A closer evaluation of processing of the APP 717 mutant, and the Swedish mutant APP by Younkin and co-workers (Suzuki et al., 1994) proved to be pivotal in providing a unified picture of these genetic Alzheimer's disease cases. In this study, not only were total levels of amyloid β production evaluated, but the specific lengths of the amyloid β peptides produced were also analyzed. The results indicated that the 717 mutation led to more than a doubling of the ratio of amyloid β 1-42 to amyloid β 1-40 (a highly soluble peptide under physiologic conditions) even though total amyloid β levels did not change. The recently discovered presenilin 1 and 2 familial Alzheimer's disease mutations in genes residing on chromosome 14 and chromosome 1, respectively, have also been linked to significant overproduction of amyloid β 1-42. (Mann et al., 1996, Schuener et al., 1996) Based on these findings, it is reasonable to theorize that the pathogenic process meditated by these distinctly different familial Alzheimer's disease mutations is the production of greater levels of amyloid β 1-42, the form of amyloid that aggregates most readily (Snyder et al., 1994), and the form that appears to seed aggregation of amyloid β to form neuritic plaques (Roher et al., 1993, Tamaoka et al., 1994).

Non-amyloid Plaque Components in Alzheimer's Disease Amyloid β is the major protein component of plaques, comprising more than 70% of the total protein. A variety of other protein components also are present, however, including α1-antichymotrypsin (ACT), heparin sulfate proteoglycans (HSPG), apolipoproteins E and J, butyrylcholinesterase (BChE), S-100B, and several complement components. While the importance of these components in the onset and progression of Alzheimer's disease has not been established, involvement of apo E isoforms in the disease has been established by genetic studies of Roses and colleagues (Strittmatter et al., 1993), who discovered that a polymorphism in the apolipoprotein E gene, namely apo E4, correlated with earlier onset of Alzheimer's disease in a large set of late-onset familial Alzheimer's disease cases. Subsequent studies have confirmed that groups of individuals with apo E4 have a significantly greater risk of Alzheimer's disease and that the onset of Alzheimer's disease roughly parallels the gene dosage for apo E4. On a mechanistic level, studies have revealed that apo E4 binds with lower affinity to amyloid β than apo E3 or apo E2, isoforms which are associated with later onset of Alzheimer's disease. It has been suggested that these isoforms may exert a protective effect by more effective clearance of amyloid β 1-41 deposits (LaDu et al., 1994, 1995).

The role of other plaque components is not as clear, though recent studies (Oda et al., 1995) have shown that apo J (clusterin) can significantly enhance the toxicity of aggregated amyloid β 1-42 in vitro. It also has been reported that HSPG enhances the toxicity of amyloid β 1-40 when injected into rat brain (Snow et al., 1992). Wright et al. (1993) demonstrated that amyloid plaques from Alzheimer's disease brain contain significant levels of BChE, while amyloid plaques from elderly non-demented individuals do not. The acute phase inflammatory protein ACT also is upregulated in Alzheimer's disease brain, and it is known to associate with the N-terminal 16 residues of amyloid β. Ma et al. have reported that ACT can enhance the aggregation of amyloid β 1-42, and these authors speculate that the enhanced aggregation contributes to its neurotoxicity.

Amyloid β Cellular Responses and In Vivo Pathology. Beyond the plaques and tangles that are the hallmarks of Alzheimer's disease, it is clear that a range of cellular responses has been induced, both in neurons and in accompanying glial cells. At a biochemical level, hyperphosphorylation of the tau protein is evident, resulting from perturbation of the kinase/phosphatase balance. At a transcriptional level, a variety of genes is activated to produce a spectrum of proteins not normally present or only present at lower levels in the brain. There also is significant evidence that inflammatory processes have been activated.

In spite of the large volume of knowledge accumulated from neuropathological and immunohistochemical studies, it is difficult to distinguish which events are associated with early, causative processes, and which are simply late stage phenomena. Presently, relatively few specific signaling processes or responses that occur in cell culture have been documented to occur in vivo, and few molecular hallmarks from Alzheimer's disease brain tissue have been shown to be activated in cultured neurons subjected to a range of possible degenerative insults likely to be involved in Alzheimer's disease. One of these processes, tau phosphorylation, has been documented to be induced by aggregated amyloid β1-42 in differentiated SH-SY5Y cells (Lambert, et al., 1994), and this result has been confirmed in a more recent report by Busciglio et al. (1995), in which amyloid β activated tau phosphorylation in cultured primary rat hippocampal neurons.

Fibrillar Amyloid β and Neurodegeneration in Alzheimer's Disease. The precise and detailed mechanism by which amyloid β 1-42 causes Alzheimer's disease has not been elucidated, but the literature contains more than 200 studies of amyloid β neurotoxicity, many of which have been reviewed recently (Yankner, 1996; Iversen et al., 1995). The consensus view that has emerged in the literature is that in order for amyloid β to be toxic, it must assemble into fibrillar structures (Pike et al., 1993). Solutions containing only monomeric amyloid β have repeatedly been demonstrated to have no deleterious effect on neurons in culture. Furthermore, studies apparently have been able to correlate the formation of amyloid β-sheet containing fibrils and the timing and extent of toxicity using techniques such as circular dichroism and electron microscopy (Simmons, et al., 1994). One study concluded explicitly that amyloid β must exist in fibrillar form in order for it to be toxic (Lorenzo and Yankner, 1994). Despite this consensus regarding amyloid β structure and activity, there continues to be a problem of reproducibility of published experimental work involving amyloid toxicity, and widespread variability of activity obtained with different batches of amyloid, or even the same batch of amyloid handled in slightly different ways, in spite of identical chemical composition (May et al., 1992). This has raised questions regarding the precise structures of amyloid β that are responsible for its activity.

BRIEF DESCRIPTION OF THE FIGURES

FIG. 1 illustrates the potency of ADDL's in inducing cell death in a brain slice assay.

FIG. 2 illustrates FACS assay of cells bound to fluorescent labeled ADDL's.

FIG. 3 illustrates the inhibition of the binding of ADDL's to B103 cells.

FIG. 4 illustrates ADDL compromised LTP response.

SUMMARY OF THE INVENTION

The invention encompasses a new composition of matter, amyloid beta-derived dementing ligands (ADDLs). ADDLs consist of amyloid β peptide assembled into non-fibrillar oligomeric structures that are capable of activating specific cellular processes. Another aspect of the invention consists of methods for assaying the formation, presence, receptor protein binding and cellular activities of ADDLs. The invention further encompasses assay methods and inhibitor molecules for cellular signaling molecules activated by ADDLs. Yet another aspect of the invention relates to molecules that block proteins that promote the formation of ADDLs, and molecules that block proteins which promote the formation of ADDLs.

DETAIL DESCRIPTION OF THE INVENTION

It has been discovered that in neurotoxic samples of amyloid β, not only did fibrillar structures exist, but that also some small globular protein structures existed. Under certain conditions, samples that contained predominantly these soluble globular protein assemblies have been generated and removal of the larger, fibrillar forms of amyloid a by centrifugation did not remove these soluble globular assemblies of amyloid β in the supernatant fractions. These supernatant fractions exhibited significantly higher neurotoxicity than unfractionated amyloid β samples aggregated under literature conditions. These neurotoxic soluble globular forms are referred to as amyloid β-derived dementing ligands (ADDLs). It has further been demonstrated that samples of amyloid β that had been "aged" for more than three weeks lost their neurotoxicity and these samples contained predominantly fibrillar structures with few or no ADDLs.

When a DMSO solution containing monomeric amyloid β 1-42 is diluted into cold F12 cell culture media, then allowed to incubate at 4° C. for 24-48 h and centrifuged for 30 minutes, 14,000 g at 4° C., the supernatant fraction contains small, soluble oligomeric globules that are highly neurotoxic in neuronal cell and brain slice cultures. The dose response curve shown in FIG. 1 demonstrates the potency of these oligomeric assemblies or ADDLs in inducing cell death in a brain slice assay as measured by the Live/Dead™ fluorescence assay (Molecular Probes, Eugene, Oreg.). Atomic force microscope analysis of such a supernatant fraction reveals a number of different size globules, with two predominant sizes of 4.9-5.3 nm and 5.7-6.2 nm that constitute ca. 70% of the structures in a typical sample. The remaining structures are monomer, dimer, and smaller numbers of oligomers in size ranges of ca. 4 nm, 8-10 nm, 15 nm, and 20 nm). Monomeric and dimeric amyloid β are not neruotoxic in neuronal cell cultures or in the organotypic brain slice cultures. By non-denaturing gel electrophoresis, the bands corresponding to the ADDLs run at 27 kD.

If the ADDLs are prepared by the incorporation of 10% biotinylated amyloid β 1-42, they can be utilized in a receptor binding assay carried out on a fluorescence activated cell sorting (FACS) instrument, with labeling by a fluorescent avidin conjugate. FIG. 2 illustrates a FACS scan involving the rat CNS B103 cells without and with ADDL incubation. This receptor binding is saturable, and brief treatment with trypsin selectively removes a subset of cell surface proteins and eliminates binding of ADDLs. FIG. 3 illustrates that this assay is useful for identifying compounds that can block the receptor binding of ADDLs. The peptide amyloid β 1-40 at 10 μM is capable of blocking ADDL binding int he receptor assay and it is capable of blocking the neurotoxic effects of ADDLs in the hippocampal brain slice assay. Proteins that are cleavable by brief treatment with trypsin from the surface of B103 cells also prevent ADDL binding to B103 cells or cultured primary rat hippocampal neurons.

When 20 nL of the ADDL preparation is injected into the hippocampal region of an adult mouse 60-70 minutes prior to the conduct of an LTP experiment (e.g. Namgung et al., 1995), the stimulation phase of the experiment occurred in a manner identical with saline control injections, but the consolidation phase showed a significant, continuing decline in synaptic activity as measured by cell body spike amplitude, over the subsequent 2 hours, compared with control animals, in which synaptic activity remained at a level comparable to that exhibited during the stimulation phase. Analysis of brain slices after the experiment indicated that no cell death had occurred. These results, shown in FIG. 4, indicate that ADDL treatment compromised the LTP response, suggesting that ADDLs are responsible for compromised learning and memory in Alzheimer's disease by interference with neuronal signaling processes, rather than by the induction of nerve cell death.

ADDLs bring about a rapid morphological change in serum starved B103 cells, and they also activate fyn kinase activity in these cells, suggesting that fyn is involved in the neurodegenerative process induced by ADDLs. This has been confirmed by experiments in brain slice cultures from genetically altered mice that lack a functional fyn gene, where addition of ADDLs resulted in no increased neurotoxicity compared to vehicle controls. Therefore, compounds that block fyn activity or localization may be important neuroprotective drugs for Alzheimer's disease.

When ADDLs are added to cultures of primary astrocytes, the astrocytes become activated and the mRNA for several proteins, including IL-1, inducible nitric oxide synthase, apo E, Apo J and α1-antichymotrypsin become elevated.

EXAMPLE 1

Preparation of Amyloid β Oligomers 1 mg of solid amyloid β1-42 is dissolved in 44 μL of anhydrous DMSO, and this 5 mM solution is diluted into cold (4° C.) F12 media (Gibco) to a total volume of 2.20 mL (50-fold dilution), and vortexed for 30 seconds. The mixture is allowed to incubate at 0° C. for 24 h, followed by centrifugation at 14,000 g for 10 minutes at 4° C. The supernatant is diluted by factors of 1:100 to 1:10,000 into the particular defined medium, prior to incubation with brain slice cultures, cell cultures or binding protein preparations. A 20 μL aliquot of the 1:100 dilution is applied to the surface of a freshly cleaved mica disk, and analyzed by atomic force microscopy. The AFM analysis is carried out on a Digital Instruments Nanoscope IIIa instrument using a J-scanner and operating in tapping mode. AFM data is analyzed using the Nanoscope IIIa software and the IGOR Pro™ waveform analysis software. Analysis by gel electrophoresis was carried out on 15% polyacrylamide gels and visualized by Coomassie blue staining.

EXAMPLE 2

Crosslinking of Amyloid β Oligomers

Oligomer preparation was carried out as described in example 1, with the following modification. The F12 media was replaced by a buffer containing the following components: N, N-dimethylglycine (766 mg/L), D-glucose (1.802 g/L), calcium chloride (33 mg/L), copper sulfate pentahydrate (25 mg/L), iron(II) sulfate heptahydrate (0.8 mg/L), potassium chloride (223 mg/L), magnesium chloride (57 mg/L), sodium chloride (7.6 g/L), sodium bicarbonate (1.18 g/L), disodium hydrogen phosphate (142 mg/L), and zinc sulfate heptahydrate (0.9 mg/L). The pH of the buffer was adjusted to 7.0 using 0.1 M sodium hydroxide. The supernatant was treated with 0.22 mL of a 25% aqueous solution of glutaraldehyde (Aldrich), followed by 0.67 mL of 0.175 M sodium borohydride in 0.1 NaOH. The mixture stirred at 4° C. for 15 min. and was quenched by addition of 1.67 mL of 20% aqueous sucrose. The mixture was concentrated 5 fold on a SpeedVac and dialyzed to remove components smaller than 1 kD. The material was analyzed by SDS PAGE and gel filtration chromatography was carried according to the following: Superose 75PC 3.2/3.0 column was equilibrated with filtered and degassed 0.15% ammonium hydrogen carbonate buffer (pH=7.8) at a flow rate of 0.02 mL/min over the course of 18 h at room temperature. The flow rate was changed to 0.04 mL/min and 20 mL of solvent was eluted. 50 microliters of reaction solution was loaded on to the column and the flow rate was resumed at 0.04 mL/min. Compound elution was monitored via UV detection at 220 nm, and 0.5-1.0 mL fractions were collected during the course of the chromatography.

EXAMPLE 3

Brain Slice Assay

An adult mouse is sacrificed by carbon dioxide inhalation, followed by rapid decapitation. The head is emersed in cold, sterile dissection buffer (94 ml Gey's balanced salt solution, pH 7.2, supplemented with 2 mL 0.5M $MgCl_2$, 2 ml 25% glucose, and 2 mL 1.0 M Hepes.), after which the brain is removed and placed on a sterile Sylgard-coated plate. The cerebellum is removed and a mid-line cut is made to separate the cerebral hemispheres. Each hemisphere is sliced separately. The hemisphere is placed with the mid-line cut down and a 30 degree slice from the dorsal side is made to orient the hemisphere. The hemisphere is glued cut side down on the plastic stage of a Campden tissue chopper (previously wiped with ethanol) and emersed in ice cold sterile buffer. Slices of 200 μm thickness are made from a lateral to medial direction, collecting those in which the hippocampus is visible. Each slice is transferred with the top end of a sterile pipette to a small petri dish containing growth medium (DMEM, 10% fetal calf serum, 2% S/P/F (streptomycin, penicillin, and fungizone Life Technologies), observed with a microscope to verify the presence of the hippocampus, and placed on a Millicell-CM insert (Millipore) in a deep well tissue culture dish (Falcon, 6-well dish). Each well contains 1.0 mL of growth medium, and usually two slices are on each insert. Slices are placed in the incubator (6% $CO_2$, 100% humidity) overnight. Growth medium is removed and wells are washed with 1.0 mL warm Hanks BSS (Life Technologies). Defined medium (DMEM, N2 supplements, SPF) containing the amyloid β oligomers, with or without inhibitor compounds, is added to each well and the incubation is continued for 24 hours. Cell death is measured using the LIVE/DEAD® assay kit (Molecular Probes, Eugene, Oreg.). This a dual-label fluorescence assay in which live cells are detected by the presence of an esterase that cleaves calcein-AM to calcein, resulting in a green fluorescence. Dead cells take up ethidium homodimer, which intercalates with DNA and has a red fluorescence. The assay is carried out according to the manufacturer's directions at 2 μM ethidium homodimer and 4 μM calcein. Images are obtained within 30 minutes using a Nikon Diaphot microscope equipped with epifluorescence. The MetaMorph image analysis system is used to quantify the number and/or area of cells showing green or red fluorescence. FIG. 1 illustrates the Dead/Live cell ratio verses ADDL concentration.

EXAMPLE 4

MTT Oxidative Stress Toxicity Assay—PC12 Cells

This assay shows the earliest detectable toxicity change in response to amyloid β oligomers. PC12 cells are passaged at $4 \times 10^4$ cell/well on a 96-well culture plate and grown for 24 hours in DMEM+10% fetal calf serum+1% S/P/F (streptomycin, penicillin, and fungizone). Plates are treated with 200 μg/mL poly-1-lysine for 2 hours prior to cell plating to enhance cell adhesion. One set of six wells is left untreated and fed with fresh media, while another set of wells is treated with the vehicle control (PBS containing 10% 0.01 N HCl, aged o/n at RT). Positive controls are treated with triton (1%) and Na Azide (0.1%) in normal growth media. Amyloid β oligomers prepared as described in Example 1, with and without inhibitor compounds present are added to the cells for 24 hours. After the 24 hour incubation, MTT (0.5 mg/mL) is added to the cells for 2.5 hours (11 μL of 5 mg/ml stock solubilized in PBS into 100 μL of media). Healthy cells reduce the MTT into a formazan blue colored product. After the incubation with MTT, the media is aspirated and 100 μL of 100% DMSO is added to lyse the cells and dissolve the blue crystals. The plate was incubated for 15 min at RT and read on a plate reader (ELISA) at 550 nm.

EXAMPLE 5

MTT Oxidative Stress Toxicity Assay—HN2 Cells

HN2 cells are passaged at $4 \times 10^4$ cells/well on a 96-well culture plate and grown for 24 hours in DMEM+10% fetal calf serum+1% S/P/F (streptomycin, penicillin, and fungizone). Plates are treated with 200 μg/mL poly 1-lysine for 2 hours prior to cell plating to enhance cell adhesion. The cells are differentiated for 24-48 hours with 5 μM retinoic acid and growth is further inhibited with 1% serum. One set of wells is left untreated and given fresh media. Another set of wells is treated with the vehicle control (0.2% DMSO). Positive controls are treated with triton (1%) and NA Azide (0.1%). Amyloid β oligomers prepared as described in Example 1, with and without inhibitor compounds present are added to the cells for 24 hours. After the 24 hour incubation, MTT (0.5 mg/mL) is added to the cells for 2.5 hours (11 μL of 5 mg/mL stock into 100 μL of media). After the incubation with MTT, the media is aspirated and 100 μL of 100% DMSO is added to lyse the cells and dissolve the blue crystals. The plate is incubated for 15 min at RT and read on a plate reader (ELISA) at 550 nm.

EXAMPLE 6

LTP Assay

Injections of intact animals: Mice are anesthetized with urethane and placed in a sterotaxic apparatus. Body temperature is maintained using a heated water jacket pad. The brain surface is exposed through holes in the skull. Bregma and lambda positions for injection into the middle molecular layer of hippocampus are 2 mm posterior to bregma, 1 mm lateral to the midline, and 1.2-1.5 mm ventral to the brain surface. Amyloid β oligomer injections are by nitrogen puff through ~10 nm diameter glass pipettes. Volumes of 20-50 nL of amyloid β oligomer solution (180 nM of amyloid β) are given over the course of an hour. The animal is allowed to rest for varying time periods before the LTP stimulus is given.

LTP in injected animals: Experiments follow the paradigm established Routtenberg and colleagues for LTP in mice (Namgung, et al., 1995). Perforant path stimulation from the entorhinal cortex is used, with recording from the middle molecular layer and the cell body of the dentate gyrus. A population excitatory postsynaptic potential (pop-EPSP) and a population spike potential (pop-spike) are observed upon electrical stimulation and LTP can be induced in these responses by a stimulus of 3 trains of 400 Hz, 8×0.4 ms pulses/train (Namgung, et al., 1995). Recordings are taken for 2-3 hours after the stimulus to determine if LTP is retained. The animal is then sacrificed immediately or is allowed to recover for either 1, 3, or 7 days and then sacrificed as above. The brain is cryoprotected with 30% sucrose and then sections (30 μM) with a microtome. Some sections are placed on slides subbed with gelatin and others are analyzed using a free-floating protocol. Immunohistochemistry is used to monitor changes in GAP-43, in PKC subtypes, and in protein phosphorylation of tau (PHF-1), paxillin, and focal adhesion kinase.

Wave forms are analyzed by machine as described previously (Colley, 1990, J. Neurosci.). A 2-way ANOVA compares changes in spike amplitude between treated and untreated groups. FIG. 2 illustrates the spike amplitude effect of ADDLs.

EXAMPLE 7

Neuronal Viability in Injected Animals

After the LTP experiment is performed, animals are allowed to remover for various times and then sacrificed using sodium pentobarbitol asesthetic and perfusion with 4% paraformaldehye. For viability studies, times of 3 hours, 24 hours, 3 days, and 7 days are used. The brain is cryoprotected with 30% sucrose and then sectioned (30 μM) with a microtome. Sections are placed on slides subbed with gelatin and stained initially with cresyl violet. Cell loss is measured by counting cell bodies in the dentate gyrus, CA3, CA1, and entorhinal cortex and is correlated with dose and time of exposure of ADDLs.

EXAMPLE 8

Cell Morphology by Phase Microscopy

Cultures are grown to low density (50-60% confluence). To initiate the experiment, the cells are serum starved in F12 media for 1 hour. Cells are then incubated for 3 hours with amyloid β oligomers prepared as described in Example 1, with and without inhibitor compounds added to the cells for 24 hours. After 3 hours, cells are examined for morphological differences or fixed for immunofluorescence labeling. Samples are examined using the MetaMorph Image Analysis system and an MRI video camera (Universal Imaging, Inc.).

EXAMPLE 9

FACScan Assay for Binding to Intact Cells

For flow cytometry, cells are dissociated with 0.1% trypsin and plated at least overnight onto tissue culture plastic at low density. Cells are removed with cold PBS/0.5 mM EDTA, washed three times and resuspended in ice-cold PBS to a final concentration of 500,000 cells/mL. Cells are incubated in cold PBS with amyloid β oligomers prepared as described in Example 1, except that 10% of the amyloid β is an amyloid β 1-42 analog containing biocytin at position 1 replacing aspartate. Oligomers with and without inhibitor compounds present are added to the cells for 24 hours. The cells are washed twice in cold PBS to remove free, unbound amyloid β oligomers and resuspended in a 1:1,000 dilution of avidin conjugated to fluorescein and incubated for one hour at 4° C. with gentle agitation. Cells are analyzed by a Becton-Dickinson Fluorescence Activated Cell Scanner (FACScan). 10,000 or 20,000 events are collected for both forward scatter (size) and fluorescence intensity, and the data are analyzed by Consort 30 software (Becton-Dickinson). An alternative procedure uses amyloid β-specific antibodies and fluorescent secondary antibody instead of avidin, eliminating the need to incorporate 10% of the biotynylated amyloid β analog. FIG. 2 illustrates the ADDL-cell binding FACS analysis, and FIG. 3 illustrates the utility of the FACS assay for identification of ADDL-blocking compounds.

These examples are intended to illustrate the present invention and not to limit it in spirit or scope.

Cai, X. D., Golde, T. E., and Younkin, S. G. (1993). Release Of Excess Amyloid Beta Protein From a Mutant Amyloid Beta Protein Precursor. *Science* 259, 514-516.

Chartier-Harlan, M. C., Crawford, F., Houlden, H., Warren, A., Hughes, D., et al (1991) Early-onset Alzheimer's Disease Caused by Mutations at Codon 717 of the B-Amyloid Precursor Protein *Nature*, 353, 844-6.

Citron, M., Oltersdorf, T., Haass, C., McConlogue, L., Hung, A. Y., Seubert, P., Vigo-Pelfrey, C., Lieberburg, I., Selkoe, D. (1992). Mutation Of the Amyloid Precursor Protein In Familial Alzheimer's Disease Increases Beta Protein Production. *Nature* 360, 672-674.

Esch, F. S., Keim, P. S., Beattie, E. C., Blacher, R. W., Culwell, A. R., Oltersdorf, T., McClure, D., Ward, P. J. (1990). Cleavage Of Amyloid Beta Peptide During Constitutive Processing Of Its Precursor *Science* 248, 1122-1124.

Glenner, G. G., and Wong, C. W. (1984a). Alzheimer's Disease Initial Report Of the Purification and Characterization Of a Novel Cerebrovascular Amyloid. *Biochem Biophys. Res Commun* 120, 885-890.

Glenner, G. G., and Wong, C. W. (1984b). Alzheimer's Disease and Downs Syndrome Sharing Of a Unique Cerebrovascular Amyloid Fibril Protein. *Biochem Biophys Res Commun* 122, 1131-1135.

Goate, A., Chartier-Harlen, M. C., Mullan, M., Brown, J., Crawford, F., et al (1991) Segregation of a Mis-sense Mutation in the Amyloid Precursor Protein Gene with Familial Alzheimer's Disease. *Nature*, 349, 704-6.

Kang, J., Lemaire, H. G., A. Unterbeck, J. Salbaum, C. Masters, K.-H. Grzeschik, G. Multhaup, K. Beyreuther, B. Muller-Hill (1987) *Nature* 325, 733.

Ladror, U. S., Snyder, S. W., Wang, G. T., Holzman, T. F., Krafft, G. A. (1994) "Cleavage at the Amino and Carboxy Termini of Alzheimer's Amyloid-β by Cathepsin D" *J. Biol. Chem.* 269, 18422-8.

Ladu, M. J., Falduto, M. T.; Manelli, A. M.; Reardon, C. A.; Getz, G. S.; Frail, D. E. (1994). Isoform-Specific Binding of Apolipoprotein-E to Beta-Amyloid. *J. Biol. Chem.* 269, 23403-23406.

LaDu, M. J., Pederson, T. M., Frail, D. E., Reardon, C. A., Getz, G. S., and Falduto, M. T. (1995). Purification of apolipoprotein E attenuates isoform-specific binding to beta-amyloid. *J. Biol. Chem.* 270, 9039-42.

Lambert, M. P., Stevens, G., Sabo, S., Barber, K., Wang, G., Wade, W., Krafft, G., Snyder, S., Holzman, T. F., Klein, W. L. 1994. "B/A4-Evoked Degeneration of Differentiated SH-SY5Y Human Neuroblastoma Cells" *J. Neurosci. Res.* 39, 377-384.

Levy-Lahad E., Wijsman E M, Nemens E, Anderson L, Goddard K A B, Weber J L, Bird T D, Schellenberg G D (1995) A Familial Alzheimer's Disease Locus on Chromosome 1. *Science* 269: 970-973.

Ma J, Yee A, Brewer H B, Das S and Potter H (1994) The amyloiassociated proteins a1-antichymotrypsin and apolipoprotein E promote the assembly of the Alzheimer B-protein into filaments. *Nature* 372, 92-94.

Masters, C. L., Multhaup, G., Simms, G., Pottgiesser, J., and Martins, R. (1985a). Neuronal Origin Of a Cerebral Amyloid. Neurofibrillary Tangles Of Alzheimer's Disease Contain the Same Protein As the Amyloid Of Plaque Cores and Blood Vessels. *Embo J.* 4, 2757-2764.

Masters, C. L., Simms, G., Weinman, N. A., Multhaup, G., and McDonald, B. (1985b). Amyloid Plaque Core Protein In Alzheimer's. *Proc Natl Acad Sci USA* 82, 4245-4249.

Mullan, M., Crawford, F. Axelman, K., Houlden, H., Lilius, L. Winblad, B., Lannfelt, L. (1992) A Pathogenic Mutation for Probable Alzheimer's-Disease in the APP Gene at the N-Terminus of Beta-Amyloid Nature Genetics 1, 345-347.

Murrell, J., Farlow, M., Ghetti, B., and Benson, M. D. (1991). A mutation in the amyloid precursor protein associated with hereditary Alzheimer's disease. *Science* 254, 97-9.

Oda, T., Pasinetti, G. M., Osterburg, H. H., Anderson, C., Johnson, S. A., Finch, C. E. "Purification and Characterization of Brain Clusterin" *Biochem. Biophys. Res. Commun.*, 1994, 204, 1131-1136.

Oda, T., Pasinetti, G. M., Stine, W. B., Snyder, S. W., Holzman, T. F., Krafft, G. A., Osterburg, H. H., Johnson, S. A., Finch, C. E. (1995) "Clusterin Inhibits Aggregation of β-Amyloid Protein and Forms Soluble Aβ/Clusterin assemblies that Induce Oxidative Stress" *Exptl. Neurology*, 136, 22-31.

Roher, A. E., Palmer, K. C., Yurewicz, E. C., Ball, M. J., Greenberg, B. D., Strittmatter, W. J., Huang, D. Y., Bhasin, R., Roses, A. D., and Goldgaber, D. (1993). Morphological and biochemical analyses of amyloid plaque core proteins purified from Alzheimer's disease brain tissue. *Neurochem.* 61, 1916-1926.

Selkoe, D. J. (1994). Normal and abnormal biology of the beta-amyloid precursor protein. Cowan, W. M. (Ed.). *Annual Review of Neuroscience*, Vol. 17. ix+623p. Annual Reviews Inc.: Palo Alto, Calif., USA., 489-517.

Sherrington R, et al., (1995) Cloning a gene bearing missense mutations in early onset familial Alzheimer's disease. *Nature* 375: 754-758.

Sisodia, S. S., Koo, E. H., Beyreuther, K., Unterbeck, A., and Price, D. L. (1990). Evidence That Beta Amyloid Protein In Alzheimer's Disease Is Not Derived By Normal Processing. *Science* 248, 492-495.

Snow, A. D., Sekiguchi, R. T., Nochlin, D., Kimata, K. "Brain amyloid accumulation in rats within 1 week of infusion of amyloid-β and a plaque component" (1992) *Soc. Neurosci. Abstr.* 18, 1465.

Snyder, S. W., Ladror, U. L., Wade, W. S., Wang, G. T., Barrett, L. W., Matayoshi, E. D., Huffaker, J. J. Krafft, G. A., Holzman, T. F. "Amyloid β Aggregation: Selective Inhibition of Aggregation in Mixtures of Amyloid with Different Lengths" *Biophys. J.* 1994, 67, 1216-28.

Suzuki, N., Cheung, T. T., Cai, X. D., Odaka, A., Otvos, L., Jr., Eckman, C., Golde, T. E., and Younkin, S. G. (1994). An increased percentage of long amyloid β protein secreted by familial amyloid protein precursor (beta-APP-717) mutants. *Science* 264, 1336-1340.

Tamaoka-A Kindo-T Odaka-A Sahara-N Sawamura-N Ozawa-K Suzuki-N Shoji-S Mori-H (1994) Biochemical-Evidence for the Long-Tail Form (A-Beta-1-42-43) of Amyloid-Beta Protein as a Seed Molecule in Cerebral Deposits of Alzheimer's Disease *Biochem. Biophys. Res. Commun.* 205, 834-842.

Tanzi, R. E., Gusella, J. F., Watkins, P. C., Bruns, G. A. P., St. George-Hyslop, P. H., van Keuren, D., Patterson, D., Pagan, S., Kurnit, D. M., and Neve, R. L. (1987). Amyloid Beta Protein Gene Complementary DNA Messenger RNA Distribution and Genetic Linkage Near the Alzheimer Locus. *Science* 235, 880-884.

Wright C I, Geula C and Mesulam M M (1993) Neuroglial cholinesterases in the normal brain and in Alzheimer's Disease: relationship to plaques, tangles and patterns of selective vulnerability. Ann Neurol 34, 373-384.

Zhang, C., Lambert, M. P., Bunch, C., Barber, K., Wade, W., Krafft, G. A., Klein, W. L. "Focal Adhesion Kinase Expressed in Nerve Cell Lines Shows Increased Tyrosine Phosphorylation in Response to Alzheimer's Aβ Peptide" *J. Biol. Chem.* 1994, 269, 25247-50.

Busciglio, J., Lorenzo, A., Yeh, J., and Yankner, B. A. (1995). beta-amyloid fibrils induce tau phosphorylation and loss of microtubule binding. *Neuron* 14, 879-88.

Iversen, L. L., Mortishire-Smith, R. J., Pollack, S. J., and Shearman, M. S. (1995). The toxicity in vitro of beta-amyloid protein. *Biochemical Journal* 311, 1-16.

Lorenzo, A., and Yankner, B. A. (1994). Beta-amyloid neurotoxicity requires fibril formation and is inhibited by congo red. *Proc. Natl. Acad. Sci. USA*, 91, 12243-7.

Mann, D. M., Iwatsubo, T., Cairns, N. J., Lantos, P. L., Nochlin, D., Sumi, S. M., Bird, T. D., Poorkaj, P., Hardy, J., Hutton, M., Prihar, G., Crook, R., Rossor, M. N., and Haltia, M. (1996). Amyloid beta protein (Abeta) deposition in chromosome 14-linked Alzheimer's disease: predominance of Abeta42(43). Annals of Neurology 40, 149-56.

May, P. C., Gitter, B. D., Waters, D. C., Simmons, L. K., Becker, G. W., Small, J. S., and Robison, P. M. (1992). beta-Amyloid peptide in vitro toxicity: lot-to-lot variability. *Neurobiology of Aging* 13, 605-7.

Namgung, U., Valcourt, E., and Routtenberg, A. (1995). Long-term potentiation in vivo in the intact mouse hippocampus. *Brain Research* 689, 85-92.

Pike, C. J., Burdick, D., Walencewicz, A. J., Glabe, C. G., and Cotman, C. W. (1993). Neurodegeneration induced by beta-amyloid peptides in vitro: the role of peptide assembly state. *Journal of Neuroscience* 13, 1676-87.

Scheuner, D., Eckman, C., Jensen, M., Song, X., Citron, M., Suzuki, N., Bird, T. D., Hardy, J., Hutton, M., Kukull, W., Larson, E., Levy-Lahad, E., Viitanen, M., Peskind, E., Poorkaj, P., Schellenberg, G., Tanzi, R., Wasco, W., Lannfelt, L., Selkoe, D., and Younkin, S. (1996). Secreted amyloid beta-protein similar to that in the senile plaques of Alzheimer's disease is increased in vivo by the presenilin 1 and 2 and APP mutations linked to familial Alzheimer's diesase. *Nature Medicine* 2, 864-70.

Simmons, L. K., May, P. C., tomaselli, K. J., Rydel, R. E., Fuson, K. S., Brigham, E. F., Wright, S., Lieberburg, I., Becker, G. W., Brems, D. N., and et al. (1994). Secondary structure of amyloid beta peptide correlates with neurotoxic activity in vitro. *Molecular Pharmacology* 45, 373-9.

Strittmatter, W. J., Saunders, A. M., Schmechel, D., Pericak-Vance, M., Enghild, J., Salvesen, G. S., and Roses, A. D. (1993). Apolipopprotein E: high-avidity binding to beta-amyloid and increased frequency of type 4 allele in late-onset familial Alzheimer disease. *Proc. Natl. Acad. Sci. USA* 90, 1977-81.

Yankner, B. A. (1996). Mechanisms of neuronal degeneration in Alzheimer's disease. *Neuron* 16, 921-32.

What is claimed:

1. A method for identifying compounds that block receptor binding of a soluble non-fibrillar amyloid β protein assembly, comprising:
   (a) mixing a test compound with a cell culture media after formation of a soluble non-fibrillar amyloid β protein assembly comprising 3-12 amyloid β proteins, wherein the amyloid β proteins are the amyloid β 1-42 protein and having neurotoxic activity;
   (b) contacting the mixture of 11(a) with B103 cells or other neuronal cells;
   (c) adding a labeled reagent that can bind to the protein assembly of 11(a); and
   (d) detecting the presence of the labeled reagent bound to the protein assembly.

2. A method for identifying compounds that block formation of a soluble non-fibrillar amyloid β protein assembly, comprising:
   (a) mixing a test compound with a cell culture media before formation of a soluble non-fibrillar amyloid β protein assembly comprising 3-12 amyloid β proteins, wherein the amyloid β proteins are the amyloid β 1-42 protein and having neurotoxic activity;

(b) contacting the mixture of 12(a) with B103 cells or other neuronal cells;
(c) adding a labeled reagent that can bind to the protein assembly of 12(a);
(d) detecting the presence of the labeled reagent bound to the protein assembly, wherein test compounds exhibiting more inhibition of receptor binding of the protein assembly when the test compound is added before the formation of the protein assembly of 12(a), compared with addition of test compounds after formation, are compounds that block formation of the protein assembly.

* * * * *

UNITED STATES PATENT AND TRADEMARK OFFICE
CERTIFICATE OF CORRECTION

PATENT NO. : 7,638,283 B2  Page 1 of 1
APPLICATION NO. : 11/130566
DATED : December 29, 2009
INVENTOR(S) : Krafft et al.

It is certified that error appears in the above-identified patent and that said Letters Patent is hereby corrected as shown below:

At column 1, line 11, please insert --This invention was made with government support under Grant Number AG 10481, nawarded by the National Institutes of Health. The government has certain rights in the invention.--

Signed and Sealed this

Fourteenth Day of September, 2010

David J. Kappos
*Director of the United States Patent and Trademark Office*

UNITED STATES PATENT AND TRADEMARK OFFICE
CERTIFICATE OF CORRECTION

| | |
|---|---|
| PATENT NO. | : 7,638,283 B2 |
| APPLICATION NO. | : 11/130566 |
| DATED | : December 29, 2009 |
| INVENTOR(S) | : Krafft et al. |

It is certified that error appears in the above-identified patent and that said Letters Patent is hereby corrected as shown below:

At column 1, line 11, please insert --This invention was made with government support under Grant Number AG 10481, awarded by the National Institutes of Health. The government has certain rights in the invention.--

This certificate supersedes the Certificate of Correction issued September 14, 2010.

Signed and Sealed this

Fourteenth Day of December, 2010

David J. Kappos
*Director of the United States Patent and Trademark Office*